(12) United States Patent
Nakamura et al.

(10) Patent No.: US 11,202,361 B2
(45) Date of Patent: Dec. 14, 2021

(54) X-RAY TUBE DEVICE

(71) Applicant: FUJIFILM Corporation, Tokyo (JP)

(72) Inventors: Kenji Nakamura, Kanagawa (JP);
Ryosuke Ogura, Kanagawa (JP);
Keiichiro Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/062,057

(22) Filed: Oct. 2, 2020

(65) Prior Publication Data

US 2021/0035769 A1 Feb. 4, 2021

Related U.S. Application Data

(63) Continuation of application No. PCT/JP2019/014810, filed on Apr. 3, 2019.

(30) Foreign Application Priority Data

Apr. 5, 2018 (JP) .............................. JP2018-073484

(51) Int. Cl.
*H05G 1/06* (2006.01)
*A61B 6/06* (2006.01)
(Continued)

(52) U.S. Cl.
CPC .................. *H05G 1/06* (2013.01); *A61B 6/06* (2013.01); *A61B 6/10* (2013.01); *G21K 1/02* (2013.01); *H01J 35/18* (2013.01)

(58) Field of Classification Search
CPC ................ H05G 1/06; A61B 6/10; A61B 6/06
See application file for complete search history.

(56) References Cited

U.S. PATENT DOCUMENTS 4,166,220 A * 8/1979 Stutts ...................... A61B 6/14
378/147
2006/0188065 A1* 8/2006 Razzano ................ A61B 6/563
378/98
(Continued)

FOREIGN PATENT DOCUMENTS

JP 4-024022 A 1/1992
JP 5-065307 U 8/1993
(Continued)

OTHER PUBLICATIONS

Communication dated Apr. 27, 2021 in Japanese Application No. 2020-512286.
(Continued)

*Primary Examiner* — Chih-Cheng Kao
(74) *Attorney, Agent, or Firm* — Sughrue Mion, PLLC

(57) ABSTRACT

An X-ray tube device includes a main body that incorporates a bulb, which generates X-rays, a collimator that is provided to protrude from the main body in an irradiation direction of the X-rays in a part of a front surface (first surface), which is a surface of the main body, and has an irradiation window for irradiating the X-rays with an adjusted irradiation range, and connectors that are provided for connecting a guard unit for keeping a distance from a test object, between the front surface (first surface) of the main body and a front surface (second surface), which is a surface of the collimator where the irradiation window is provided.

9 Claims, 5 Drawing Sheets

(51) Int. Cl.
*A61B 6/10* (2006.01)
*H01J 35/18* (2006.01)
*G21K 1/02* (2006.01)

(56) References Cited

U.S. PATENT DOCUMENTS

| | | | |
|---|---|---|---|
| 2012/0093298 A1 | 4/2012 | Lalena | |
| 2014/0098938 A1 | 4/2014 | Nishimura | |
| 2014/0105360 A1* | 4/2014 | Yamanaka | A61B 6/4405 |
| | | | 378/62 |
| 2014/0133627 A1* | 5/2014 | Sakuragi | A61B 6/4429 |
| | | | 378/62 |
| 2019/0029619 A1* | 1/2019 | Ogura | A61B 6/4405 |

FOREIGN PATENT DOCUMENTS

| | | | | |
|---|---|---|---|---|
| JP | 2011-030699 | A | 2/2011 | |
| JP | 2011-253727 | A | 12/2011 | |
| JP | 2014-073310 | A | 4/2014 | |
| JP | 2014-079518 | A | 5/2014 | |
| JP | 2014-110872 | A | 6/2014 | |
| JP | 2015-128521 | A | 7/2015 | |
| JP | 2016-047308 | A | 4/2016 | |
| JP | 6006897 | B1 * | 10/2016 | A61B 6/4405 |
| JP | 2017-185106 | A | 10/2017 | |

OTHER PUBLICATIONS

International Search Report dated Jul. 9, 2019 in International Application No. PCT/JP2019/014810.
Written Opinion of the International Searching Authority dated Jul. 9, 2019 in International Application No. PCT/JP2019/014810.
International Preliminary Report on Patentability dated Oct. 6, 2020 in International Application No. PCT/JP2019/014810.

* cited by examiner

X-RAY TUBE DEVICE

CROSS-REFERENCE TO RELATED APPLICATIONS

This application is a Continuation of PCT International Application No. PCT/JP2019/014810 filed on Apr. 3, 2019, which claims priority under 35 U.S.C § 119 (a) to Japanese Patent Application No. 2018-073484 filed on Apr. 5, 2018. The above application is hereby expressly incorporated by reference, in its entirety, into the present application.

BACKGROUND OF THE INVENTION

1. Field of the Invention

The present invention relates to an X-ray tube device.

2. Description of the Related Art

An X-ray tube device is a device that generates X-rays, and incorporates a bulb (so-called X-ray tube) that generates the X-rays. In the X-ray tube device, there are an example where a handle that protrudes to a test object side is provided in an X-ray movable stop (JP2016-047308A), an example where a protection cover is provided on a test object side of an X-ray generator (JP2011-030699A), and an example where a cover (cover unit) is provided around an X-ray source or the like (JP2014-079518A). There is an example where a guide unit that protrudes from an X-ray source to keep a distance between the X-ray source and a test object constant is provided (JP2014-110872A, corresponding to US2014/0133627A1).

In addition, in a portable X-ray tube device in which an X-ray tube device is independently movable for round or the like, there is a case where a member for operation, gripping, or keeping an interval from a subject is provided in a front surface (a surface facing the subject) of a collimator. For example, PX-20HF plus manufactured by Kenko Tokina Corporation, or the like has a collimator that is rotatable about an irradiation direction of X-rays, and is provided with a handle (or a guide unit) that protrudes in the irradiation direction of the X-rays in a front surface of the collimator. IPF-21N manufactured by Canon Inc. is provided with a handle (or a guide unit) that protrudes in an irradiation direction of X-rays in a front surface of a housing having a substantially cube shape in which an X-ray tube and a collimator are integrated.

SUMMARY OF THE INVENTION

In the X-ray tube device, there is a case where a guard unit that sets a distance between the X-ray tube device and the test object to be equal to or longer than a specific distance determined in advance is provided. However, in a case where the X-ray tube device is reduced in size, there is no space for providing the guard unit, and there is a problem in that the guard unit cannot be attached even where necessary. Accordingly, an object of the invention is to provide an X-ray tube device that allows a guard unit to be attached thereto even though the X-ray tube device is reduced in size.

An X-ray tube device according to an aspect of the invention comprises a main body that incorporates a bulb, which generates X-rays, a collimator that is provided to protrude from the main body in an irradiation direction of the X-rays in a part of a first surface, which is a surface of the main body, and has an irradiation window for irradiating the X-rays with an adjusted irradiation range, and connectors that are provided for connecting a guard unit for keeping a distance from a test object, between the first surface of the main body and a second surface, which is a surface of the collimator where the irradiation window is provided.

It is preferable that the connectors are provided in the collimator.

It is preferable that the connectors have a shape in which a length in a direction perpendicular to the irradiation direction of the X-rays is longer than a length in a direction parallel to the irradiation direction of the X-rays.

It is preferable that the X-ray tube device comprises the guard unit connected to the connectors.

It is preferable that the guard unit comprises a first pillar portion, a second pillar portion, a third pillar portion, and a fourth pillar portion extending in the irradiation direction from the second surface of the collimator, a first beam portion that connects the first pillar portion and the fourth pillar portion on the test object side than the second surface, a second beam portion that connects the second pillar portion and the third pillar portion on the test object side than the second surface, a third beam portion that connects the first pillar portion and the second pillar portion on the first surface side than the second surface, and a fourth beam portion that connects the third pillar portion and the fourth pillar portion on the first surface side than the second surface.

It is preferable that the guard unit has a shape in which an interval between the first pillar portion and the second pillar portion and an interval between the third pillar portion and the fourth pillar portion spread in the irradiation direction of the X-rays.

It is preferable that the guard unit is configured such that the first pillar portion and the fourth pillar portion are parallel to each other, and the second pillar portion and the third pillar portion are parallel to each other.

It is preferable that the guard unit has the connectors in the third beam portion and the fourth beam portion.

It is preferable that, in a case where the main body has a rectangular parallelepiped shape, the first beam portion connects the first pillar portion and the fourth pillar portion in a transverse direction of the first surface, the second beam portion connects the second pillar portion and the third pillar portion in the transverse direction of the first surface, the third beam portion connects the first pillar portion and the second pillar portion in a longitudinal direction of the first surface, and the fourth beam portion connects the third pillar portion and the fourth pillar portion in the longitudinal direction of the first surface.

It is preferable that, in a case where the main body has a rectangular parallelepiped shape, in comparison in a longitudinal direction of the first surface, the guard unit is longer than the collimator, and the guard unit is shorter than the main body.

The X-ray tube device according to the aspect of the invention can provide a small X-ray tube to which the guard unit can be attached.

DESCRIPTION OF THE PREFERRED EMBODIMENTS

Figure 1:
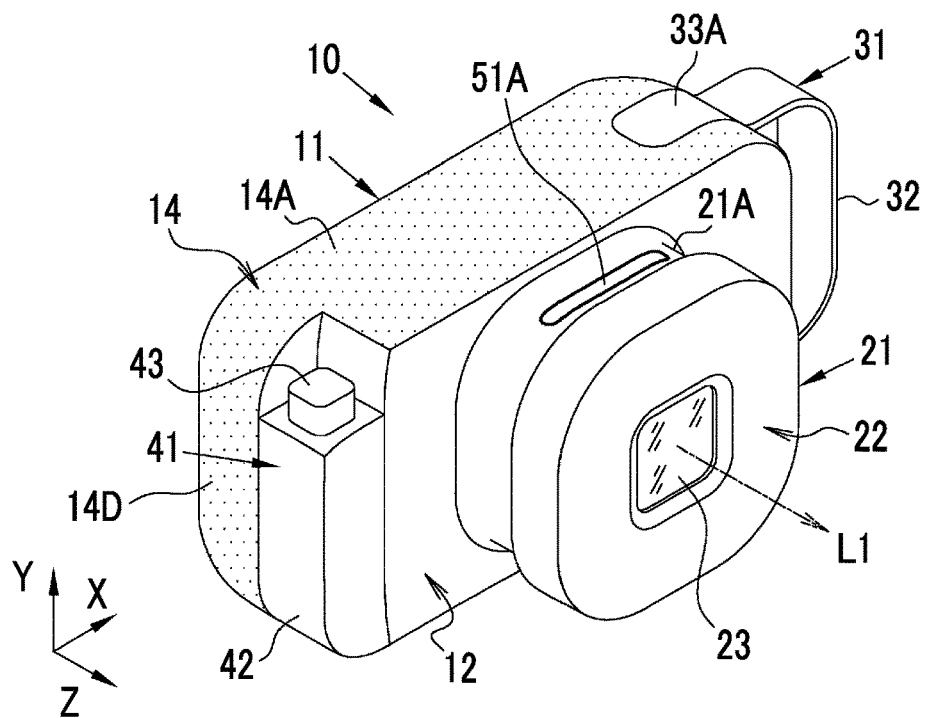
FIG. 1 is a perspective view of an X-ray tube device.
Figure 2:
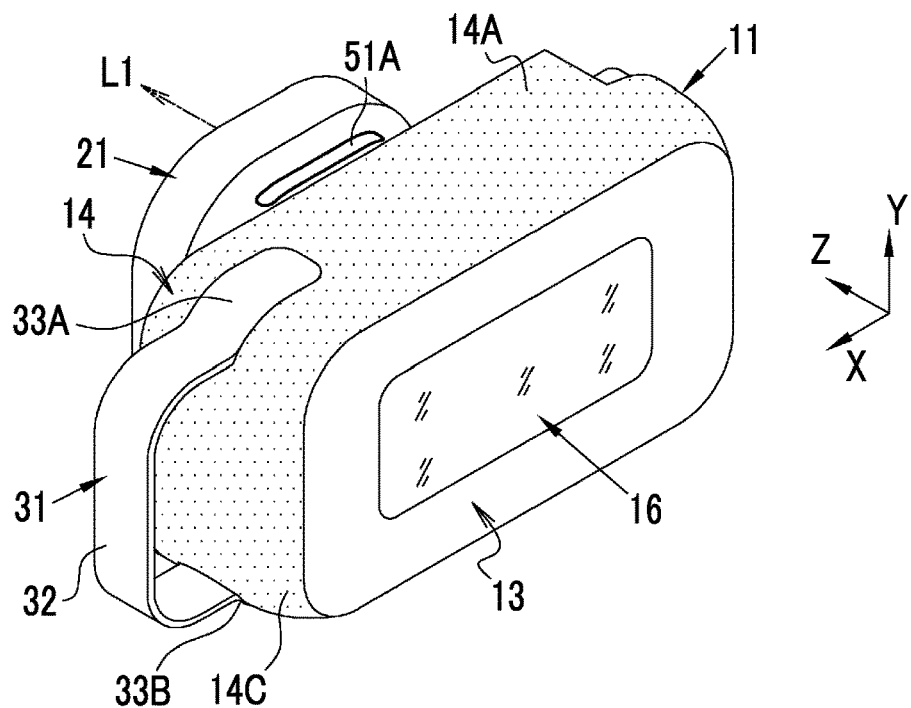
FIG. 2 is a perspective view of the X-ray tube device.

As shown in FIGS. 1 and 2, an X-ray tube device 10 comprises a main body 11, a collimator 21, a gripping portion 31, a switch 41, and the like.

The main body 11 incorporates a bulb 17 (see FIG. 3) that generates at least X-rays. In the embodiment, the main body 11 has a substantially rectangular parallelepiped shape. The substantially "rectangular parallelepiped shape" refers to that an appearance is formed by three sets of planes substantially parallel to each other, and the surfaces of the respective sets are substantially connected at 90 degrees. The substantially "rectangular parallelepiped shape" includes a case where connection portions of the surfaces of the respective sets are chamfered or the surfaces of the respective sets are connected with curved surfaces.

Hereinafter, an irradiation direction L1 of the X-rays in the X-ray tube device 10 is referred to as a Z direction, a longitudinal direction of the main body 11 that is a direction substantially perpendicular to the Z direction is referred to as an X direction, and a transverse direction of the main body 11 that is a direction substantially perpendicular to the Z direction and the X direction is referred to as a Y direction. The irradiation direction L1 of the X-rays in which a test object (not shown) is disposed is a positive direction of the Z direction, a side on which the gripping portion 31 is provided along the longitudinal direction of the main body 11 is a positive direction of the X direction, and a positive direction of the Y direction is determined such that the X direction, the Y direction, and the Z direction constitute a so-called right-handed system.

A surface facing the test object among the surfaces of the main body 11, that is, a surface in which the collimator 21 is provided is a front surface 12 (first surface) of the main body 11. Accordingly, among the surfaces of the main body 11, the front surface 12 is a surface for irradiating the X-rays. Then, among the surfaces of the main body 11, a surface that faces the front surface 12 and is substantially parallel to the front surface 12 is a rear surface 13 of the main body 11. In the rear surface 13, an operating unit 16 that is used for setting, operation, and the like of the X-ray tube device 10 is provided (see FIG. 2). In the embodiment, although the operating unit 16 is a touch panel, the operating unit 16 can be constituted using at least one of buttons, switches, a display, or the like.

Among the surfaces of the main body 11, a surface that connects the front surface 12 and the rear surface 13 is a side surface 14 of the main body 11. That is, a surface excluding the front surface 12 and the rear surface 13 among the surfaces of the main body 11 is the side surface 14. In a case where the main body 11 is a substantially rectangular parallelepiped, the side surface 14 has an upper surface 14A and a lower surface 14B that face each other and are substantially parallel to each other, and a right surface 14C and a left surface 14D that face each other and are substantially parallel to each other.

The upper surface 14A is a portion in the side surface 14 that is visible in a case where the X-ray tube device 10 is viewed from a positive side in the Y direction. The lower surface 14B is a portion in the side surface 14 that is visible in a case where the X-ray tube device 10 is viewed from a negative side in the Y direction. The right surface 14C is a portion in the side surface 14 that is visible in a case where the X-ray tube device 10 is viewed from a positive side in the X direction. Similarly, the left surface 14D is a portion in the side surface 14 that is visible in a case where the X-ray tube device 10 is viewed from a negative side in the X direction. Accordingly, the upper surface 14A may partially overlap at least one of the right surface 14C or the left surface 14D. Similarly, the lower surface 14B may partially overlap at least one of the right surface 14C or the left surface 14D. The right surface 14C may partially overlap at least one of the upper surface 14A or the lower surface 14B, and the left surface 14D may partially overlap at least one of the upper surface 14A or the lower surface 14B. In the definition of each surface, it is assumed that a portion of the collimator 21 or the like hidden by a portion protruding from the main body 11 is included in the "visible portion".

Figure 3:
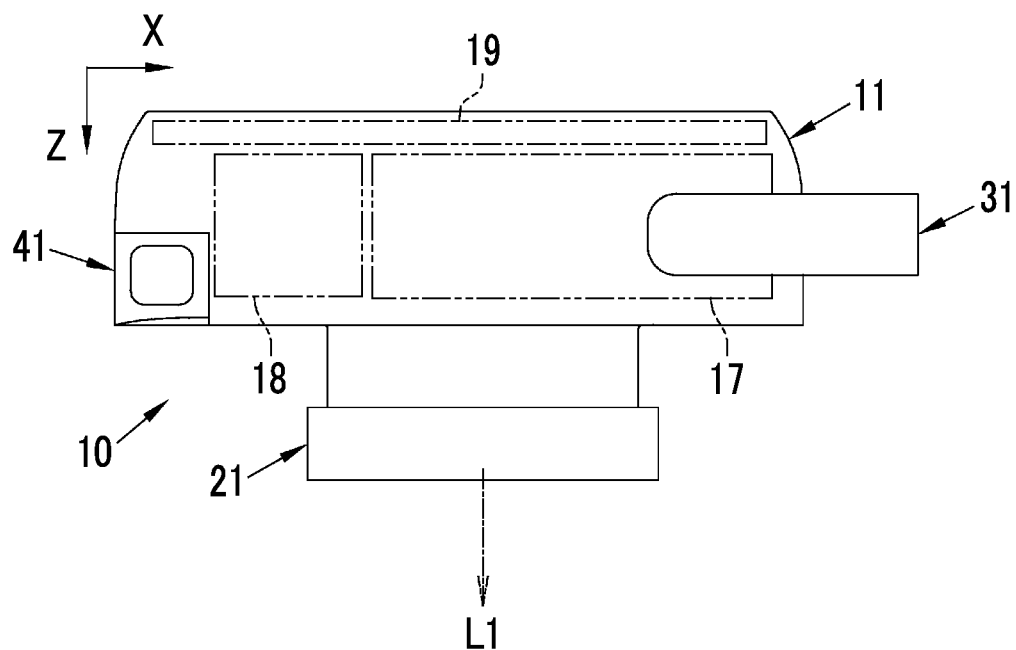
FIG. 3 is an explanatory view showing an example of incorporated parts of the main body.

As shown in FIG. 3, the main body 11 of the embodiment incorporates a battery 18, a control circuit 19, and the like, in addition to the bulb 17 that generates the X-rays. The battery 18 supplies electric power necessary for operation to the bulb 17, the control circuit 19, and the like. The control circuit 19 controls the operation of the main body 11. That is, the control circuit 19 controls a tube voltage, a tube current, an X-ray generation (irradiation) timing, and the like of the bulb 17. The main body 11 can be provided with a plug, a cord, and the like that are connected to a power supply (not shown), which supplies electric power to the respective units of the main body 11, instead of the battery 18 or in addition to mounting of the battery 18. Although the bulb 17 is an X-ray tube that generates the X-rays, the main body 11 can be mounted with a bulb that generates radiation other than X-rays, instead of the bulb 17 that is the X-ray tube. In this case, the X-ray tube device 10 constitutes a so-called radiation generation device according to the kind of radiation generated by the bulb.

The collimator 21 is provided to protrude from the main body 11 in the irradiation direction L1 (Z direction) of the X-rays in a part of the front surface 12 (first surface), which is a surface of the main body 11, and has an irradiation window 23 for irradiating the X-rays with an adjusted irradiation range. The reason that the collimator 21 is formed in a shape protruding in "a part" of the front surface 12 of the main body 11 is to reduce the size, such as the appearance and volume of the X-ray tube device 10. In a case where the entire front surface 12 of the main body 11 protrudes and the main body 11 is in a shape in which the collimator 21 is included inside the main body 11, the entire volume of the main body 11, consequently, the X-ray tube device 10 increases. The irradiation range of the X-rays is a shape of the X-rays that reach an X-ray imaging panel or the like, an area of the X-rays, a position of the X-rays with respect to the X-ray tube device 10, and the like. While the X-rays generated by the bulb 17 are cone beams that spread in a conical shape, an imaging surface of the X-ray imaging panel generally has a rectangular shape. For this reason, the collimator 21 adjusts, for example, the cone beams generated by the bulb 17 in a quadrangular pyramid shape in conformity with the imaging surface of the X-ray imaging panel and irradiates the cone beams from the irradiation window 23. As a result, the collimator 21 suppresses wasteful exposure of the test object. The irradiation window 23 is formed of a material that can transmit at least the X-rays without waste. A surface (second surface) where the irradiation window 23 is provided is a front surface 22 of the collimator 21. The collimator 21 incorporates one or a plurality of X-ray shielding members (not shown) and comprises an operating unit (not shown) that adjusts the internal arrangement (an inclination and the like) of the X-ray shielding members in order to adjust the irradiation range of the X-rays.

In a case where the portion of the collimator 21 is reduced in size in order to reduce the size of the entire X-ray tube device 10, the collimator 21 has a base end portion 21A having a diameter smaller than a distal end portion. The base end portion 21A of the collimator 21 is a portion on the front surface 12 side of the main body 11, and the distal end portion of the collimator 21 is a portion on the test object side. The reason that the collimator 21 is formed in the above-described shape in a case of reducing the size of the collimator 21 is because the X-rays spread in the irradiation direction L1.

The gripping portion 31 is provided to protrude from the main body 11 in the side surface 14, and is a handle that supports the main body 11 (and the entire X-ray tube device 10) by gripping. The gripping portion 31 is provided on the right surface 14C side of the main body 11. The user can support the main body 11 in a posture necessary for imaging, for example, even with one hand and can easily keep the posture by gripping the gripping portion 31.

The gripping portion 31 is connected to the main body 11 at one place or two places. In the embodiment, the gripping portion 31 is connected to the main body 11 at two places of a connection point 33A and a connection point 33B. For this reason, the gripping portion 31 and the right surface 14C that is the side surface 14 of the main body 11 form a loop shape. The connection point 33A is a connection point to at least one of the upper surface 14A or the right surface 14C of the main body 11. The connection point 33B is a connection point to at least one of the lower surface 14B or the right surface 14C of the main body 11.

In the gripping portion 31, a flat plate portion 32 that is present between the connection point 33A and the connection point 33B is a standard gripping position. Unless there is a need to keep the X-ray tube device 10 in a special posture, normally, the user can easily support the posture of the X-ray tube device 10 in a posture necessary for imaging by gripping the flat plate portion 32. In the embodiment, although the flat plate portion 32 is a flat plate shape, the flat plate portion 32 may be formed in any shape. The flat plate portion 32 can be formed, for example, in a curved or more stereoscopic grip shape.

The switch 41 inputs at least one of an irradiation preparation instruction of the X-rays or an irradiation start instruction of the X-rays to the X-ray tube device 10. In the embodiment, the switch 41 is attachably and detachably provided in a corner portion of the main body 11 that is a left end (an end on the negative side in the X direction) of the front surface 12 of the main body 11 and an end of the left surface 14D on the front surface 12 side. The switch 41 is connected to the main body 11 in a wired or wireless manner, and can input the irradiation start instruction or the like and can transmit and receive other control signals even in a state in which the switch 41 is detached from the main body 11 as well as in a state in which the switch 41 is attached to the main body 11. Furthermore, the switch 41 can transmit or receive a synchronization signal to or from the X-ray imaging panel through the main body 11 or directly and can synchronously control the X-ray tube device 10 and the X-ray imaging panel. Synchronization regarding the operation includes a case where the operation is performed with a delay of a specific time.

The switch 41 comprises a support 42, and a button 43 that can perform a press operation. In a case where the switch 41 is attached to the main body 11, a surface of the support 42 is smoothly connected to the surface of the main body 11, such as the front surface 12 and the left surface 14D. For this reason, the switch 41 is integrated with the main body 11. On the other hand, in a case where the switch 41 is detached from the main body 11, the support 42 is a gripping portion that is used for gripping the switch 41. The button 43 is pressed in a case of inputting the irradiation start instruction or the like to the main body 11. The button 43 can perform, for example, a two-step press operation of a first step of a press operation to input the irradiation preparation instruction of the X-rays to the main body 11 and a second step of a press operation to input the irradiation start instruction in order to actually irradiates the X-rays after irradiation of the X-rays is enabled.

Figure 4:
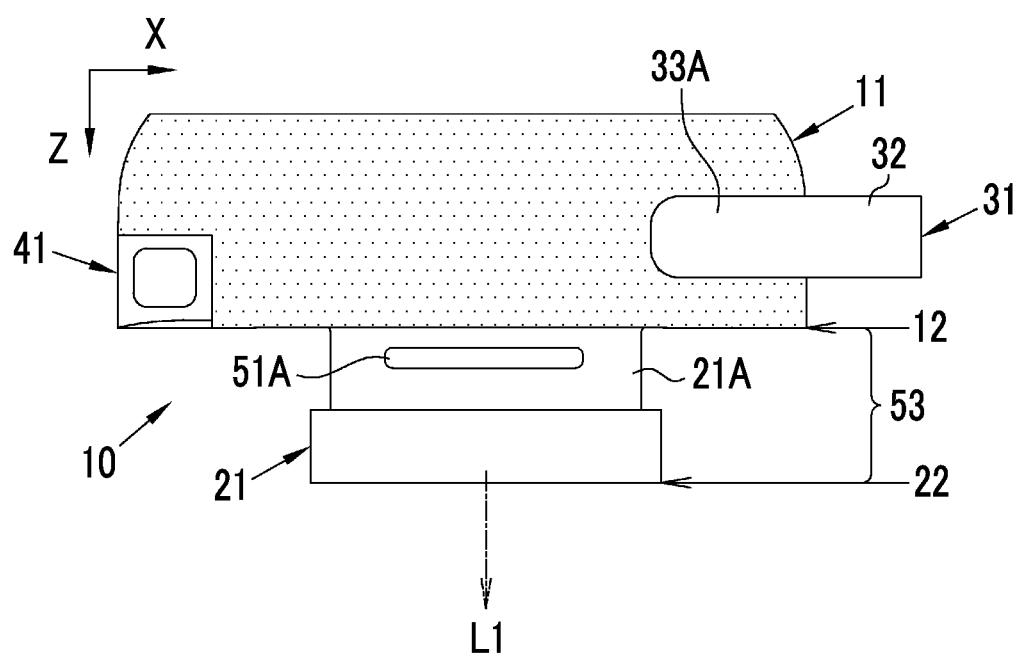
FIG. 4 is a top view of the X-ray tube device.
Figure 5:
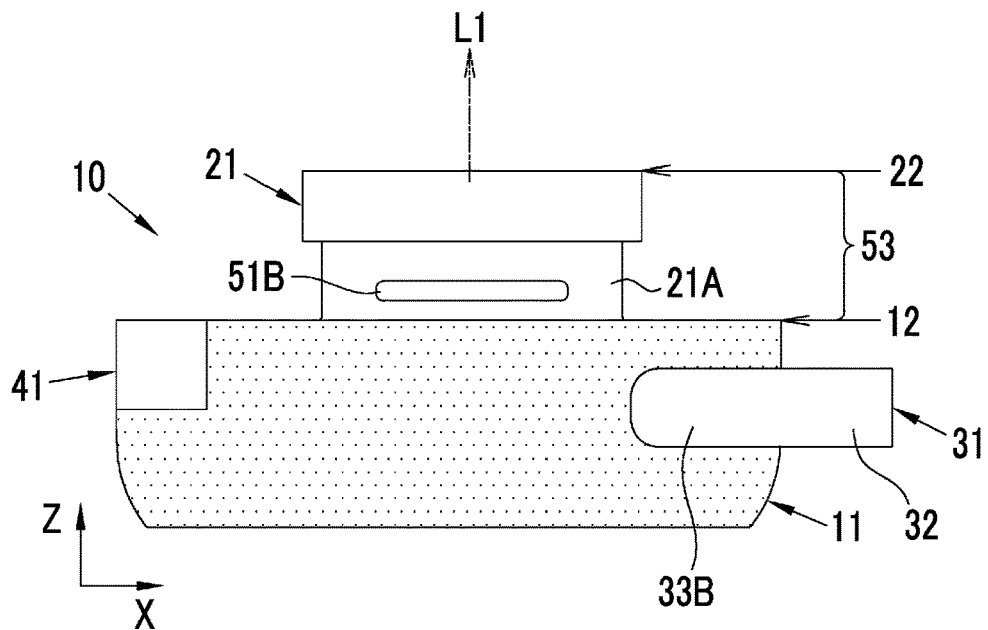
FIG. 5 is a bottom view of the X-ray tube device.

In addition, the X-ray tube device 10 comprises connectors 51A and 51B that are provided for connecting a guard unit 61 (see FIG. 6) for keeping a distance from the test object, between the front surface 12 (first surface) of the main body 11 and the front surface 22 (second surface), which is the surface of the collimator 21 where the irradiation window 23 is provided. In the embodiment, the connector 51A and the connector 51B are provided in the collimator 21. Specifically, as shown in FIGS. 4 and 5, in a range 53 between the front surface 12 of the main body 11 and the front surface 22 of the collimator 21, the connector 51A and the connector 51B are provided at two places of an upper surface (a portion that is visible in a case where the X-ray tube device 10 is viewed from the negative side in the Y direction) and a lower surface (a portion that is visible in a case where the X-ray tube device 10 is viewed from the positive side in the Y direction) of the base end portion 21A of the collimator 21, respectively.

The connector 51A and the connector 51B have a shape to be longer in a direction perpendicular to the irradiation direction of the X-rays than in a direction parallel to the irradiation direction L1 of the X-rays. This is because connection strength to the guard unit 61 is kept high compared to other shapes. In a case where the connector 51A and the connector 51B are formed in the above-described shape, even though impact or the like is applied to the connected guard unit 61, the guard unit 61 is hardly detached and the connector 51A and the connector 51B are hardly damaged or the like. The same applies to a case where the connector 51A and the connector 51B are provided in other side surfaces (portions that are visible in a case where the X-ray tube device 10 is viewed from the X direction or the Y direction) of the collimator 21. Not only in a case where the connector 51A and the connector 51B are connected to the guard unit 61 in a form of fitting, engagement, or the like, but also in a case where the connector 51A and the connector 51B are bonded to the guard unit 61 by screwing, welding, adhesion, or the like in a part of the connector 51A and the connector 51B, a similar effect to the above is obtained by forming the connector 51A and the connector 51B in the above-described shape.

As described above, the connector 51A and the connector 51B that are connected to the guard unit 61 are provided between the front surface 12 of the main body 11 and the front surface 22 of the collimator 21, whereby the X-ray tube device 10 can solve a problem that the guard unit 61 is hardly attached while achieving reduction in size as a whole.

Specifically, in a case where the X-ray tube device 10 is reduced in size, since the area of the front surface 22 of the collimator 21 inevitably decreases, connectors for attaching the guard unit 61 are hardly provided in the front surface 22 of the collimator 21. In a case where the X-ray tube device 10 is reduced in size, even though it seems that there is a space for providing the connector 51A and the connector 51B in the front surface 22 of the collimator 21, the connector 51A and the connector 51B may not be actually provided in the front surface 22 of the collimator 21 according to conditions, such as the arrangement of the X-ray shielding members inside the collimator 21. On the other hand, since the base end portion 21A of the collimator 21 is closer to the bulb 17 than the front surface 22 of the collimator 21, a spread width of the X-rays generated by the bulb 17 is relatively small. For this reason, the X-ray tube device 10 provides the connectors between the front surface 12 of the main body 11 and the front surface 22 of the collimator 21, not in the front surface 22 of the collimator 21, thereby allowing the guard unit 61 to be attached thereto even though the X-ray tube device 10 is reduced in size.

In a case where an outer wall of the collimator 21 is made of resin for reduction in weight of the X-ray tube device 10, even though the connector 51A and the connector 51B to the guard unit 61 are provided in the front surface 22 of the collimator 21, the connection strength of the guard unit 61 may be insufficient. This is because the connectors should be subject to the weight of the guard unit 61, impact applied to the guard unit 61, and the like with a very small area. In view of this point, since the X-ray tube device 10 provides the connector 51A and the connector 51B between the front surface 12 of the main body 11 and the front surface 22 of the collimator 21, it is possible to provide the connector 51A and the connector 51B having an area and a shape sufficient capable of sustaining the guard unit 61, impact applied to the guard unit 61, and the like.

In addition, in reducing the size of the X-ray tube device 10, in a case where the connector 51A and the connector 51B to the guard unit 61 are provided in the front surface 22 of the collimator 21, the distance between the X-ray tube device 10 and the test object may not be kept at a necessary constant distance even though the guard unit 61 is provided. This is because the guard unit 61 and the irradiation window 23 inevitably become close, causing an amount of the guard unit 61 capable of protruding from the front surface 22 of the collimator 21 to easily overlap the irradiation range of the X-rays. In view of this point, compared to a case where the guard unit is attached to the front surface 22 of the collimator 21, the X-ray tube device 10 can make the guard unit 61 protrude from the side of the collimator 21, that is, from a position relatively far from the irradiation window 23. As a result, even though the X-ray tube device 10 is reduced in size, it is possible to secure a necessary and sufficient protrusion amount of the guard unit 61.

Figure 6:
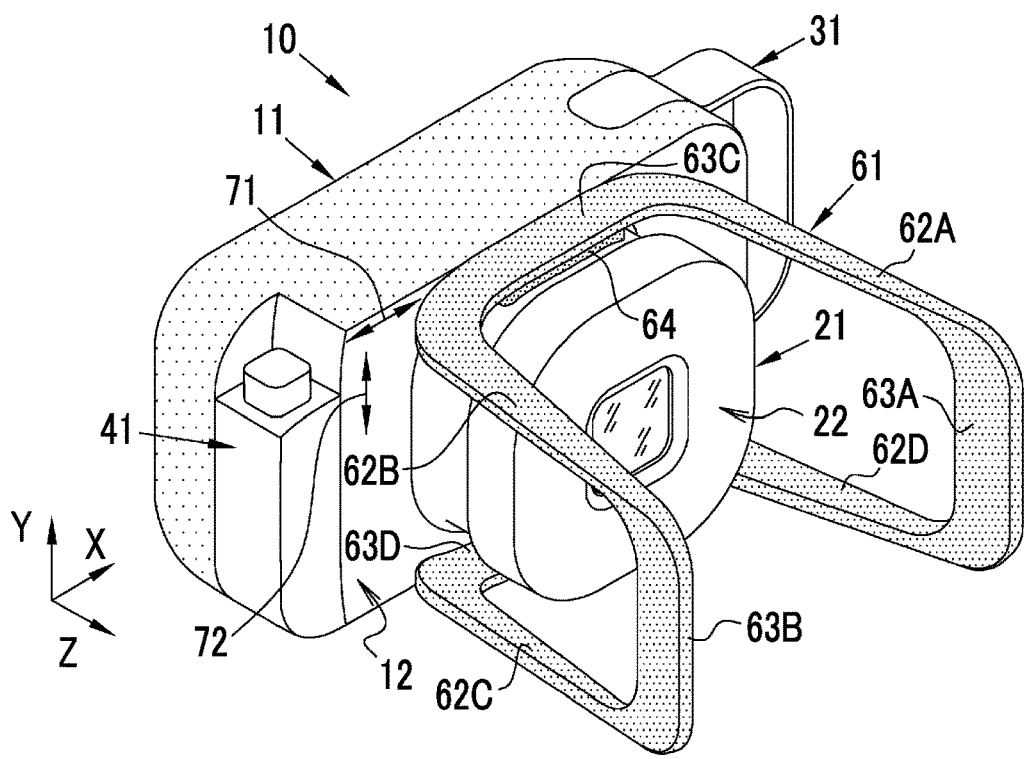
FIG. 6 is a perspective view of the X-ray tube device to which a guard unit is attached.

For example, as shown in FIG. 6, the guard unit 61 that is connected to the X-ray tube device 10 using the connector 51A and the connector 51B has a first pillar portion 62A, a second pillar portion 62B, a third pillar portion 62C, and a fourth pillar portion 62D. The guard unit 61 has a first beam portion 63A, a second beam portion 63B, a third beam portion 63C, and a fourth beam portion 63D that connect two of the first pillar portion 62A, the second pillar portion 62B, the third pillar portion 62C, and the fourth pillar portion 62D to each other.

The first pillar portion 62A, the second pillar portion 62B, the third pillar portion 62C, and the fourth pillar portion 62D are portions in the guard unit 61 extending in the irradiation direction L1 of the X-rays from the front surface 22 (second surface) of the collimator 21. The portions cross at least a position (an XY plane including the front surface 22) of the front surface 22 of the collimator 21 in a case where the X-ray tube device 10 is viewed from the side (the X direction or the Y direction).

The first pillar portion 62A is a portion in the guard unit 61 extending substantially in the Z direction on the positive side in the X direction and the positive side in the Y direction of the collimator 21. The second pillar portion 62B is a portion in the guard unit 61 extending substantially in the Z direction on the negative side in the X direction and the positive side in the Y direction of the collimator 21. The third pillar portion 62C is a portion in the guard unit 61 extending substantially in the Z direction on the negative side in the X direction and the negative side in the Y direction of the collimator 21. Similarly, the fourth pillar portion 62D is a portion in the guard unit 61 extending substantially in the Z direction on the positive side in the X direction and the negative side in the Y direction of the collimator 21.

The first beam portion 63A, the second beam portion 63B, the third beam portion 63C, and the fourth beam portion 63D connect two of the pillar portions 62A to 62D in the direction (that is, substantially the X direction or the Y direction) perpendicular to the irradiation direction L1 of the X-rays.

The first beam portion 63A connects the first pillar portion 62A and the fourth pillar portion 62D on the test object side (the positive side in the Z direction) than the front surface 22 of the collimator 21 substantially in the Y direction. That is, in a case where the main body 11 has a rectangular parallelepiped shape, the first beam portion 63A connects the first pillar portion 62A and the fourth pillar portion 62D substantially in parallel with a transverse direction 72 of the front surface 12 of the main body 11. The first beam portion 63A connects distal end portions of the first pillar portion 62A and the fourth pillar portion 62D on the positive side in the Z direction. For this reason, the first pillar portion 62A and the fourth pillar portion 62D do not protrude to the test object side than the first beam portion 63A.

The second beam portion 63B connects the second pillar portion 62B and the third pillar portion 62C substantially in the Y direction on the test object side than the front surface 22 of the collimator 21. That is, in a case where the main body 11 has a rectangular parallelepiped shape, the second beam portion 63B connects the second pillar portion 62B and the third pillar portion 62C substantially in parallel with the transverse direction 72 of the front surface 12 of the main body 11. The second beam portion 63B connects distal end portions of the second pillar portion 62B and the third pillar portion 62C on the positive side in the Z direction. For this reason, the second pillar portion 62B and the third pillar portion 62C do not protrude to the test object side than the second beam portion 63B.

The third beam portion 63C connects the first pillar portion 62A and the second pillar portion 62B substantially in the X direction on the front surface 12 (first surface) side of the main body 11 than the front surface 22 of the collimator 21. That is, in a case where the main body 11 has a rectangular parallelepiped shape, the third beam portion 63C connects the first pillar portion 62A and the second pillar portion 62B substantially in parallel with a longitudinal direction 71 of the front surface 12 of the main body 11. The third beam portion 63C connects distal end portions of the first pillar portion 62A and the second pillar portion 62B on the negative side in the Z direction. The third beam portion 63C provides a guard unit-side connector 64, which is connected to the connector 51A, at a predetermined position (a position capable of being bonded to the connector 51A) in an inner surface (a surface on the collimator 21 side). In a case where the guard unit-side connector 64 is provided in the third beam portion 63C, since the entire connector 51A is supported by the third beam portion 63C, and impact or the like can be absorbed by the third beam portion 63C, at least one of connection strength or the impact resistance of the guard unit 61 is excellent.

The fourth beam portion 63D connects the third pillar portion 62C and the fourth pillar portion 62D substantially in the X direction on the front surface 12 side of the main body 11 than the front surface 22 of the collimator 21. That is, in a case where the main body 11 has a rectangular parallelepiped shape, the fourth beam portion 63D connects the third pillar portion 62C and the fourth pillar portion 62D substantially in parallel with the longitudinal direction 71 of the front surface 12 of the main body 11. The fourth beam portion 63D connects distal end portions of the third pillar portion 62C and the fourth pillar portion 62D on the negative side in the Z direction. The fourth beam portion 63D has a guard unit-side connector (not shown), which is connected to the connector 51B, at a predetermined position (a position capable of being bonded to the connector 51B) in an inner surface (a surface on the collimator 21 side). In a case where the guard unit-side connector is provided in the fourth beam portion 63D, since the entire connector 51B is supported by the fourth beam portion 63D, and impact or the like can be absorbed by the fourth beam portion 63D, at least one of connection strength or impact resistance of the guard unit 61 is excellent.

The guard unit 61 having the above-described shape is relatively excellent in impact resistance (impact absorption) or the like among guard units having various shapes that can be connected to the connector 51A and the connector 51B of the X-ray tube device 10. Furthermore, the guard unit 61, the connector 51A, and the like are hardly deteriorated due to repetitive use.

Figure 7:
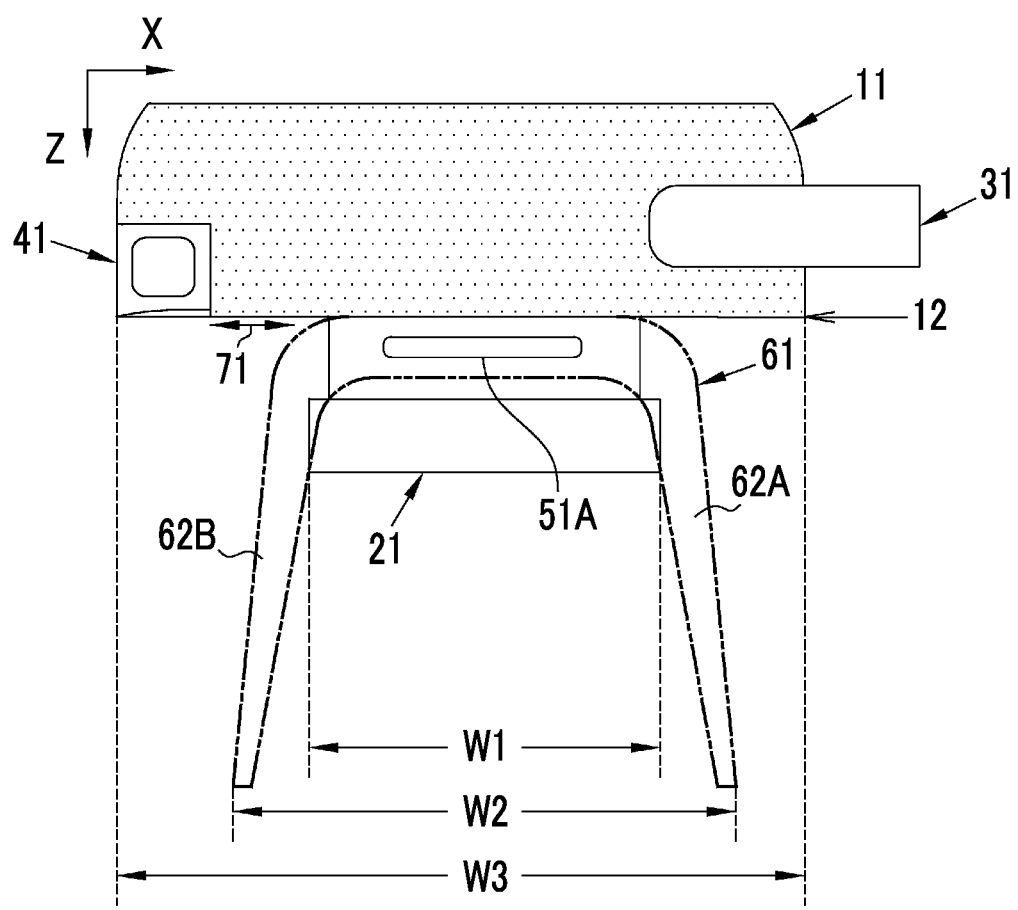
FIG. 7 is a top view of the X-ray tube device to which a guard unit is attached.

As shown in FIG. 7, the guard unit 61 has a shape in which an interval between the first pillar portion 62A and the second pillar portion 62B spreads in the irradiation direction L1 (to the positive side in the Z direction) of the X-rays. The same applies to an interval between the third pillar portion 62C and the fourth pillar portion 62D. The reason that the guard unit 61 has the shape in which the interval between the first pillar portion 62A and the second pillar portion 62B and the interval between the third pillar portion 62C and the fourth pillar portion 62D spread in the irradiation direction L1 of the X-rays in this way is because the guard unit is relatively excellent in impact resistance (impact absorption) or the like among the guard units having various shapes capable of being connected to the connector 51A and the connector 51B of the X-ray tube device 10. Furthermore, it is possible to reduce impact applied to the test object when the guard unit 61 is brought into contact with the test object. In addition, compared to a case where the interval between the first pillar portion 62A and the second pillar portion 62B and the interval between the third pillar portion 62C and the fourth pillar portion 62D are constant or a case where the interval between the first pillar portion 62A and the second pillar portion 62B and the interval between the third pillar portion 62C and the fourth pillar portion 62D are tapered in the irradiation direction L1 of the X-rays, there is an advantage that the irradiation direction L1 of the X-rays is easily directed toward the test object even though the X-ray tube device 10 is placed on an examination table or the like in a vertical orientation (in an orientation bringing the left surface 14D into contact with the examination table or the like).

In a case where the main body 11 has a rectangular parallelepiped shape, in comparison in the longitudinal direction 71 of the front surface 12 of the main body 11, a length (width W2) of the guard unit 61 may be longer than a length (width W1) of the collimator 21, and the length (width W2) of the guard unit 61 may be shorter than a length (width W3) of the main body 11 (see FIG. 7). This is because, in using the X-ray tube device 10, the guard unit 61 is not obstructive, in a case where the guard unit 61 is brought into contact with the test object or the like, a load applied to the connector 51A and the connector 51B is small, and the distance from the test object can be kept at a necessary distance.

Figure 8:
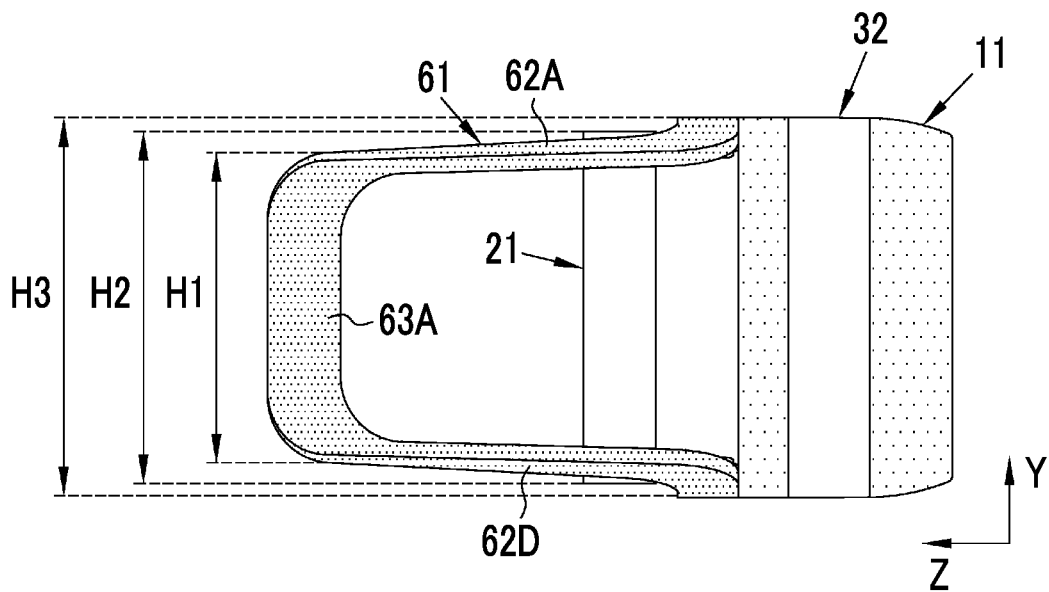
FIG. 8 is a side view of the X-ray tube device to which a guard unit is attached.

As shown in FIG. 8, the guard unit 61 is configured such that the interval between the first pillar portion 62A and the fourth pillar portion 62D is substantially constant in the irradiation direction L1 of the X-rays, and the first pillar portion 62A and the fourth pillar portion 62D are substantially parallel to each other. The same applies to the interval between the second pillar portion 62B and the third pillar portion 62C. The reason that the interval between the first pillar portion 62A and the fourth pillar portion 62D and the interval between the second pillar portion 62B and the third pillar portion 62C are substantially constant in this way is because the irradiation direction L1 of the X-rays is easily directed toward the test object in a case where the X-ray tube device 10 is placed on the examination table or the like in a horizontal orientation (in an orientation bringing the lower surface 14B into contact with the examination table or the like).

In a case where the main body 11 has a rectangular parallelepiped shape, in comparison in the transverse direction 72 of the front surface 12 of the main body 11, a length (height H2) of the guard unit 61 may be longer than a length (height H1) of the collimator 21, and the length (height H2) of the guard unit 61 may be shorter than a length (height H3) of the main body 11 (see FIG. 8). This is because, in using the X-ray tube device 10, the guard unit 61 is not obstructive, and the distance from the test object can be kept at a necessary distance.

Figure 9:
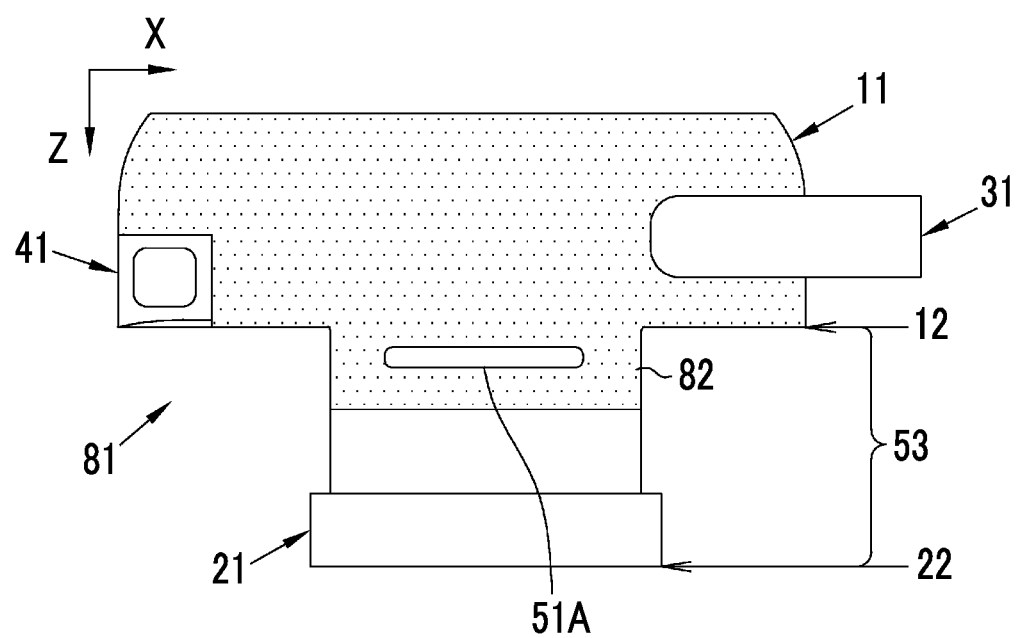
FIG. 9 is an explanatory view showing a main body shape of an X-ray tube device in a modification example.

In the above-described embodiment, although the connector 51A and the connector 51B are provided in the base end portion 21A of the collimator 21, the connector 51A and the connector 51B can be provided in the main body 11. For example, like an X-ray tube device 81 shown in FIG. 9, in a case where the main body 11 has a convex portion 82 in a portion where the collimator 21 is provided, the convex portion 82 belongs to the range 53 between the front surface 12 of the main body 11 and the front surface 22 of the collimator 21. For this reason, the connector 51A and the connector 51B can be provided in the convex portion 82 that is a part of the main body 11.

EXPLANATION OF REFERENCES

10: X-ray tube device
11: main body
12: front surface of main body
13: rear surface
14: side surface
14A: upper surface
14B: lower surface
14C: right surface
14D: left surface 16: operating unit
17: bulb
18: battery
19: control circuit
21: collimator
21A: base end portion
22: front surface of collimator
23: irradiation window
31: gripping portion
32: flat plate portion
33A, 33B: connection point
41: switch
42: support
43: button
51A, 51B: connector
53: range
61: guard unit
62A: first pillar portion
62B: second pillar portion
62C: third pillar portion
62D: fourth pillar portion
63A: first beam portion
63B: second beam portion
63C: third beam portion
63D: fourth beam portion
64: guard unit-side connector
71: longitudinal direction
72: transverse direction
81: X-ray tube device
82: convex portion
L1: irradiation direction of X-ray
W1, W2, W3: width

What is claimed is:

1. An X-ray tube device comprising:
a main body that incorporates a bulb, which generates X-rays;
a collimator that is provided to protrude from the main body in an irradiation direction of the X-rays in a part of a first surface, which is a surface of the main body, and has an irradiation window for irradiating the X-rays with an adjusted irradiation range; and
connectors that are provided for connecting a guard unit for keeping a distance from a test object, between the first surface of the main body and a second surface, which is a surface of the collimator where the irradiation window is provided, and the guard unit is connected to the connectors,
wherein the guard unit comprises
a first pillar portion, a second pillar portion, a third pillar portion, and a fourth pillar portion extending in the irradiation direction from the second surface of the collimator,
a first beam portion that connects the first pillar portion and the fourth pillar portion on the test object side relative to the second surface,
a second beam portion that connects the second pillar portion and the third pillar portion on the test object side relative to the second surface,
a third beam portion that connects the first pillar portion and the second pillar portion on the first surface side relative to the second surface, and
a fourth beam portion that connects the third pillar portion and the fourth pillar portion on the first surface side relative to the second surface.

2. The X-ray tube device according to claim 1, wherein the connectors are provided in the collimator.

3. The X-ray tube device according to claim 1, wherein the connectors have a shape in which a length in a direction perpendicular to the irradiation direction of the X-rays is longer than a length in a direction parallel to the irradiation direction of the X-rays.

4. The X-ray tube device according to claim 2, wherein the connectors have a shape in which a length in a direction perpendicular to the irradiation direction of the X-rays is longer than a length in a direction parallel to the irradiation direction of the X-rays.

5. The X-ray tube device according to claim 1, wherein the guard unit has a shape in which an interval between the first pillar portion and the second pillar portion and an interval between the third pillar portion and the fourth pillar portion spread in the irradiation direction of the X-rays.

6. The X-ray tube device according to claim 5, wherein the guard unit is configured such that the first pillar portion and the fourth pillar portion are parallel to each other, and the second pillar portion and the third pillar portion are parallel to each other.

7. The X-ray tube device according to claim 1, wherein the guard unit has the connectors in the third beam portion and the fourth beam portion.

8. The X-ray tube device according to claim 1, wherein, in a case where the main body has a rectangular parallelepiped shape,
the first beam portion connects the first pillar portion and the fourth pillar portion in a transverse direction of the first surface,
the second beam portion connects the second pillar portion and the third pillar portion in the transverse direction of the first surface,
the third beam portion connects the first pillar portion and the second pillar portion in a longitudinal direction of the first surface, and
the fourth beam portion connects the third pillar portion and the fourth pillar portion in the longitudinal direction of the first surface.

9. The X-ray tube device according to claim 1, wherein, in a case where the main body has a rectangular parallelepiped shape, in comparison to a longitudinal direction of the first surface, the guard unit is longer than the collimator, and the guard unit is shorter than the main body.

* * * * *